(12) United States Patent
Oguchi (10) Patent No.: US 8,802,889 B2
(45) Date of Patent: Aug. 12, 2014

(54) PROCESS FOR PRODUCTION OF ALLYL ACETATE

(75) Inventor: Wataru Oguchi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 13/820,323

(22) PCT Filed: Sep. 20, 2011

(86) PCT No.: PCT/JP2011/071944
§ 371 (c)(1),
(2), (4) Date: Mar. 1, 2013

(87) PCT Pub. No.: WO2012/039506
PCT Pub. Date: Mar. 29, 2012

(65) Prior Publication Data
US 2013/0172602 A1 Jul. 4, 2013

(30) Foreign Application Priority Data
Sep. 21, 2010 (JP) .................. 2010-210776

(51) Int. Cl.
*C07C 67/05* (2006.01)
*C07C 69/52* (2006.01)
*C07C 67/48* (2006.01)
*C07C 67/055* (2006.01)
*C07C 69/533* (2006.01)

(52) U.S. Cl.
CPC ............. *C07C 67/055* (2013.01); *C07C 69/533* (2013.01); *C07C 67/48* (2013.01)
USPC ............................ 560/245; 560/205; 560/218

(58) Field of Classification Search
USPC .......................................... 560/245, 205, 218
See application file for complete search history.

(56) References Cited

FOREIGN PATENT DOCUMENTS

| | | |
|---|---|---|
| GB | 1 298 929 A | 12/1972 |
| JP | 61-238759 A | 10/1986 |
| JP | 1-199924 A | 8/1989 |
| JP | 11514675 A | 12/1999 |
| JP | 2001-079400 A | 3/2001 |
| WO | 9805620 A1 | 2/1998 |

OTHER PUBLICATIONS

International Search Report for PCT/JP2011/071944 dated Dec. 5, 2011.
Communication dated May 27, 2014 from the Japanese Patent Office in counterpart Japanese Patent Application No. 2010-210776.

*Primary Examiner* — Jafar Parsa
*Assistant Examiner* — Amy C Bonaparte
(74) *Attorney, Agent, or Firm* — Sughrue Mion, PLLC

(57) ABSTRACT

A process for production of allyl acetate includes steps of reacting acetic acid 3, oxygen 1 and propylene 2 in the presence of a catalyst in an oxidation reactor 5 to form allyl acetate and water; separating the unreacted acetic acid by a distillation column 9; and recovering an acetic acid-containing liquid which contains acetic acid and returning the acetic acid-containing liquid to the oxidation reactor 5 via an acetic acid-water evaporator 4, the process further including a heating step of heating a process liquid which contains the acetic acid-containing liquid to a temperature of 80 to 250° C. by a heater.

7 Claims, 3 Drawing Sheets

PROCESS FOR PRODUCTION OF ALLYL ACETATE

CROSS REFERENCE TO RELATED APPLICATIONS

This application is a National Stage of International Application No. PCT/JP2011/071944 filed Sep. 20, 2011 (claiming priority based on Japanese Patent Application No. 2010-210776, filed Sep. 21, 2010), the contents of which are incorporated herein by reference in their entirety.

BACKGROUND OF THE INVENTION

1. Field of the Invention

The present invention relates to a process for production of allyl acetate by reacting oxygen, acetic acid and propylene in the presence of a catalyst.

2. Description of the Related Art

Allyl acetate is an important industrial material used in the production of solvents, pharmaceuticals, agricultural chemicals and allyl alcohol. Also, demands for allyl alcohol as a raw material of various organic chemical products such as 1,4-butanediol, tetrahydrofuran and epichlorohydrinhave recently been increasing. Therefore, a technology for efficiently producing allyl acetate and allyl alcohol has made progress in development.

As a process for producing allyl acetate, a process for reacting oxygen, acetic acid and propylene in the presence of a catalyst is widely known. There are also many reports on a process for producing allyl alcohol by further hydrolyzing the allyl acetate thus obtained.

For example, Japanese Unexamined Patent Application, First Publication No. Sho 61-238759 discloses a process for producing allyl alcohol in which oxygen, acetic acid and propylene are reacted in a vapor phase in the presence of a catalyst obtained by depositing metallic palladium and an alkali metal acetate on silica to produce allyl acetate, and then a hydrolysis reaction of allyl acetate is performed in the presence of an acidic ion-exchange resin. Japanese Unexamined Patent Application, First Publication No. Hei 1-199924 discloses a process for producing allyl acetate and allyl alcohol, and the literature describes that, in the case of producing allyl acetate, a raw material usage rate upon production of allyl acetate is improved by adjusting the concentration of allyl alcohol in a reaction raw material gas to 100 ppm or less.

As described above, various proposals have been made regarding the process for producing allyl acetate and allyl alcohol. However, these processes do still not have sufficient industrial productivity and, particularly, activity, selectivity and lifetime of a catalyst used in the case of producing allyl acetate by a reaction of oxygen, acetic acid and propylene may often be problematic.

In light of the above circumstances, some proposals have recently been made so as to solve these problems associated with an allyl acetate production catalyst and a process for producing allyl acetate.

For example, Japanese Unexamined Patent Application, First Publication No. 2001-79400 discloses that a catalyst containing metallic palladium as a main catalyst, and tin and alkaline metals or alkaline earth metal compounds as co-catalyst components, supported on a carrier, has activity and also maintains high catalytic activity and catalyst selectivity.

However, according to the present inventors' study, it has become apparent that a decrease in activity is recognized in the catalyst disclosed in Japanese Unexamined Patent Application, First Publication No. 2001-79400 and, particularly, the catalyst drastically deteriorates when the unreacted acetic acid is recovered and recycled in the reaction, and thus there is a limitation in terms of industrial utilization.

SUMMARY OF THE INVENTION

Under these circumstances, the present invention has been made and an object thereof is to provide a process which prevents a decrease in activity and selectivity of the catalyst and improves lifetime of the catalyst, in the case of producing allyl acetate by the reaction of oxygen, acetic acid and propylene in the presence of a catalyst, when the unreacted acetic acid and also acetic acid, that is by-produced in the case of hydrolyzing allyl acetate to obtain allyl alcohol, are recovered and recycled as a raw material for producing allyl acetate.

The present inventors have intensively studied so as to achieve the above object and conceived that, when the unreacted acetic acid and also an acetic acid-containing liquid which contains acetic acid, that is by-produced in the case of hydrolyzing allyl acetate to obtain allyl alcohol, are recovered and recycled for the reaction, the unsaturated compounds such as allyl acrylate and acrylic acid, which exist as impurities in the acetic acid-containing liquid and serve as a catalyst poison, can be converted into a high-boiling-point component by a reaction (polymerization) by a heating step of treating an acetic acid-containing liquid at specific temperature in a heater. Since such a high-boiling-point component and acetic acid largely differs in a boiling point, the high-boiling-point component can be easily separated from acetic acid by simple distillation using a heater or an acetic acid-water evaporator. Therefore, it is possible to return the acetic acid-containing liquid, from which the unsaturated compound has been removed, to the reaction by performing the heating step, and to prevent deterioration of the catalyst.

That is, the present invention is directed to processes for producing allyl acetate described in the following [1] to [8].

[1] A process for producing allyl acetate, which includes the steps of reacting acetic acid, oxygen and propylene in the presence of a catalyst in a reactor to produce allyl acetate and water; separating the unreacted acetic acid by a distillation column; and recovering an acetic acid-containing liquid which contains acetic acid and returning the acetic acid-containing liquid to the reactor via an acetic acid-water evaporator, the process further including a heating step of heating a process liquid which contains the acetic acid-containing liquid to a temperature of 80 to 250° C. by a heater.

[2] The process for producing allyl acetate according to [1], wherein the process liquid is the bottom liquid of the acetic acid-water evaporator.

[3] The process for producing allyl acetate according to [1] or [2], wherein an evaporator is used as the heater.

[4] The process for producing allyl acetate according to any one of [1] to [3], wherein the process liquid after the heating step is returned to the distillation column.

[5] The process for producing allyl acetate according to any one of [1] to [4], including the step of hydrolyzing the allyl acetate, wherein the acetic acid-containing liquid contains acetic acid formed by the hydrolysis.

[6] The process for producing allyl acetate according to [5], wherein the distillation column separates acetic acid formed by the hydrolysis.

[7] The process for producing allyl acetate according to any one of [1] to [6], wherein a heating temperature in the heater is from 100° C. to 150° C.

[8] The process for producing allyl acetate according to any one of [1] to [7], wherein a residence time in the heater is 5.0 minutes or more.

According to the present invention, in the case of producing allyl acetate by the reaction of oxygen, acetic acid and propylene in the presence of a catalyst, when the unreacted acetic acid and also acetic acid, that is by-produced in the case of hydrolyzing allyl acetate to obtain allyl alcohol, are recovered and recycled as a raw material for producing allyl acetate, a decrease in activity and selectivity of the catalyst can be prevented and lifetime of the catalyst can be improved.

DETAILED DESCRIPTION OF THE INVENTION

Embodiments of the present invention will be described in detail below with reference to the accompanying drawings.

In a process for producing allyl acetate of the present embodiment, oxygen, acetic acid and propylene are reacted in the presence of a catalyst to form allyl acetate and water. The reaction scheme of this reaction is shown below.

(Raw Material)

There is no particular limitation as to propylene and oxygen gas used as the raw material. Although a lower saturated hydrocarbon such as propane or ethane may be mixed with propylene, high-purity propylene is preferably used. Oxygen gas may be diluted with an inert gas such as a nitrogen or carbon dioxide gas and may be, for example, air. When a reactant gas is circulated and reused, it is preferable to use high-purity oxygen gas, and particularly preferable to use oxygen gas having purity of 99% or more.

(Catalyst)

The catalyst may be any catalyst as long as it is capable of reacting with propylene, acetic acid and oxygen to produce allyl acetate. Preferably, it is a supporting solid catalyst in which the following components (a) to (c) are supported on a carrier (d).

(a) Palladium
(b) A compound containing at least one or more kinds of elements selected from the group of gold, copper, lead, ruthenium and rhenium
(c) At least one or more compounds selected from alkali metal acetates and alkali earth metal acetates
(a) Palladium Palladium as the component (a) may be palladium having any valence, and is preferably metallic palladium. As used herein, "metallic palladium" is palladium having a valence of 0. The metallic palladium is obtained by reducing divalent and/or tetravalent palladium ions using a reducing agent such as hydrazine or hydrogen. In this case, the entire palladium may not be in a metal state.

There is no particular limitation on a specific starting material of the component (a). It is possible to use, in addition to metallic palladium, a palladium salt which can be converted into metallic palladium. Examples of the palladium salt which can be converted into metallic palladium include, but are not limited to, palladium chloride, palladium sodium chloride, palladium nitrate and palladium sulfate.

A ratio of the palladium (a) to the carrier (d) in the catalyst, (a):(d), is preferably from 1:10 to 1:1,000, and more preferably from 1:20 to 1:500, in terms of mass ratio.

Component (b)

It is possible to use, as the component (b), soluble salts such as a nitrate, a carbonate, a sulfate, an organic acid salt and a halide, which contain at least one or more kinds of elements selected from the group of gold, copper, lead, ruthenium and rhenium. Examples of preferable elements among the above elements include gold and copper. Examples of a precursor of gold include, but are not limited to, gold chloride, gold sodium chloride, gold potassium chloride and the like. Examples of a precursor of copper include, but are not limited to, cuprous chloride, cupric chloride, copper acetate, copper nitrate, copper acetylacetonate, copper sulfate and the like.

A ratio of the component (a) to the component (b), (a):(b), is preferably from 1:0.01 to 1:10, and more preferably from 1:0.02 to 1:5, in terms of mass ratio. When the component (b) contains a plurality of elements, a ratio of each of these respective elements to the component (a), (a):(b), is preferably from 1:0.01 to 1:10, and more preferably from 1:0.02 to 1:5.

Component (c)

The component (c) is preferably an alkali metal acetate. More specifically, acetates of lithium, sodium and potassium are exemplified. It is more preferably sodium acetate and potassium acetate, and most preferably potassium acetate.

There is no particular limitation on the support amount of the alkali metal acetate and alkali earth metal acetate, and the support amount is preferably from 1 to 30 parts by mass based on 100 parts by mass of the carrier. In order to adjust to the desired support amount, the alkali metal acetate may be added to a reactor, for example, in the form of an aqueous solution or a solution of acetic acid by adding to a feed gas.

(d) Carrier

There is no particular limitation on a carrier on which the above respective catalyst components are supported, and the carrier may be a porous substance which is generally used as the carrier. Preferably, the carrier is silica, alumina, silica-alumina, diatomaceous earth, montmorillonite, titania or the like, and more preferably silica. There is no particular limitation on a shape of the carrier. Specific examples of the shape include, but are not limited to, a powder shape, a spherical shape, a pellet shape and the like.

There is no particular limitation on a particle diameter of the above carrier, and the particle diameter is preferably from 1 to 10 mm, and more preferably from 3 to 8 mm. In the case a tubular reactor is used as the reactor for producing allyl acetate and a reaction is performed by packing the reactor with the catalyst, when the particle diameter is less than 1 mm, a high pressure loss arises when a gas is circulated, and it may become impossible to effectively circulate the gas. When the particle diameter is more than 10 mm, it becomes difficult for a raw material gas to diffuse into the catalyst, and thus a catalytic reaction may not effectively proceed.

A pore structure of the above carrier preferably has a pore diameter between 1 nm and 1,000 nm, and more preferably between 2 nm and 800 nm.

There is no particular limitation on the process used for supporting the components (a), (b) and (c) on the carrier (d), and any suitable process may be used.

Specific examples of the process include a process in which a carrier is impregnated with an aqueous solution of the component (a) such as a palladium salt and the component (b)

and then treated with an aqueous solution of an alkali metal salt. In this case, it is preferable to treat with an aqueous alkali metal salt solution without drying the carrier impregnated with the catalyst solution. The treatment time with the aqueous alkali metal salt solution is the time required for the salt of the catalyst component, with which the carrier was impregnated, to be completely converted into a compound which is insoluble in water, and 20 hours is usually sufficient.

Next, the metal salt of the catalyst component precipitated on a surface layer of a catalyst carrier is converted into a 0-valent metal by treating with a reducing agent. The reduction is performed in a liquid phase by the addition of a reducing agent such as hydrazine or formalin. Thereafter, the catalyst carrier is washed with water until chlorine ions and the like are not detected, then dried, and an alkali metal acetate is supported thereon, followed by further drying.

(Reaction)

There is no particular limitation on a reaction form when a reaction between acetic acid, propylene and oxygen is performed in the presence of the catalyst, and a conventionally known reaction form can be selected. Generally, there is an optimum process according to the catalyst to be used, and therefore the reaction is preferably performed in the reaction form according to the catalyst. In the case of using a supporting solid catalyst, it is advantageous to employ a fixed bed flow reaction in which a reactor is packed with the catalyst.

There is no particular limitation on the material of the reactor for producing allyl acetate (hereinafter may sometimes be referred to as an oxidation reactor), and a reactor constituted of a material having corrosion resistance is preferable.

There is no particular limitation on a reaction temperature at which allyl acetate is produced, and the reaction temperature is preferably from 100 to 300° C., and more preferably from 120 to 250° C.

There is no particular limitation on the reaction pressure, and the reaction pressure is advantageously from 0.0 to 3.0 MPaG from the viewpoint of facility capabilities, and more preferably from 0.1 to 1.5 MPaG. "G" denotes a gauge pressure.

The raw material gas to be fed to the oxidation reactor contains at least acetic acid, propylene and oxygen, and, if necessary, it can further contain a nitrogen gas, a carbon dioxide gas, a rare gas or the like as a diluent. Acetic acid is fed to the oxidation reactor in the amount of 4 to 20% by volume, and preferably 6 to 15% by volume, in an evaporated state, based on the total amount of the raw material gas. Propylene is fed to the oxidation reactor in the amount of 5 to 50% by volume, and preferably 10 to 40% by volume, in an evaporated state, based on the total amount of the raw material gas.

A ratio (molar ratio) of acetic acid, propylene and oxygen, acetic acid:propylene:oxygen, is preferably from 1:0.25 to 13:0.15 to 4, and more preferably from 1:1 to 7:0.5 to 2.

The raw material gas is preferably passed through the catalyst in a standard state at a space velocity of 10 to 15,000 hour$^{-1}$, and particularly preferably 300 to 8,000 hour$^{-1}$.

(Production Process of Allyl Acetate)

Figure 1:
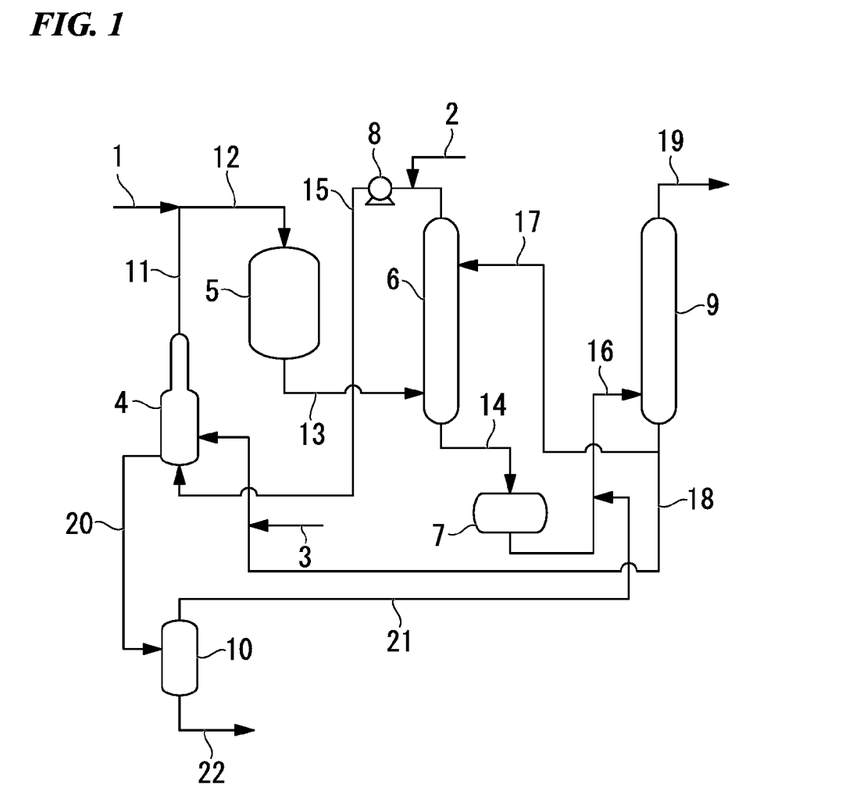
FIG. 1 is a process diagram showing an example of a production process of the present invention.

A process for producing allyl acetate of the present embodiment is shown in FIG. 1.

In the present invention, an "acetic acid-containing liquid which contains acetic acid" contains, in addition to acetic acid, impurities such as acrylic acid. It may sometimes be referred simply to as an "acetic acid-containing liquid".

In FIG. 1, 5 denotes an oxidation reactor and this oxidation reactor 5 is packed with the above-mentioned catalyst, and also a raw material gas 12 containing oxygen 1, propylene 2 and acetic acid 3 is fed thereto and allyl acetate is produced under the above-mentioned reaction conditions. A reactor outlet gas 13, which contains allyl acetate, leaving the oxidation reactor 5 is transferred to a gas-liquid separator 6, where a condensed component (containing allyl acetate, acetic acid and water as main components) contained in the reactor outlet gas 13 is obtained as a bottom liquid 14 of the gas-liquid separator column. The bottom liquid 14 of the gas-liquid separator column is delivered to a middle tank 7 and then fed to a first distillation column 9 as a feed liquid 16.

In the first distillation column 9, the liquid is separated into produced allyl acetate and the unreacted acetic acid. Specifically, the liquid is separated into a top liquid 19 of the first distillation column, which contains allyl acetate and water as main components, and a bottom liquid of the first distillation column, which contains the unreacted acetic acid and water as main components. The top liquid 19 of the first distillation column is purified to the required purity in an allyl acetate purification step (not shown).

A bottom liquid (for recovery) 18 of the first distillation column as a part of the bottom liquid of the first distillation column is recovered as an acetic acid-containing liquid which contains the unreacted acetic acid, and then fed to an acetic acid-water evaporator 4 for evaporating the raw material gas by heating, arranged at an up-stream side of the oxidation reactor 5. A part of the bottom liquid of the first distillation column is optionally fed, as a bottom liquid (for absorption) 17 of the first distillation column, to the gas-liquid separator 6 as absorption water.

Into the acetic acid-water evaporator 4, a circulation gas 15 containing a gas component (containing a diluent) from the gas-liquid separator 6 and propylene 2 is introduced after adjusting to a predetermined pressure by a compressor 8, and acetic acid 3 is also introduced. From the acetic acid-water evaporator 4, a part of the bottom liquid thereof is drawn out as an outlet liquid 20 from a bottom of the acetic acid-water evaporator, and then fed to a heater 10 where a heating step is performed.

In the heater 10, the outlet liquid 20 from a bottom of the acetic acid-water evaporator, that is, a process liquid containing the acetic acid-containing liquid is heated at a temperature within a range from 80 to 250° C., whereby, the unsaturated compounds such as allyl acrylate and acrylic acid, which are contained in the liquid 20 as impurities and serve as a catalyst poison undergo a reaction (polymerization) to produce a high-boiling-point component (heating step). The high-boiling-point component composed of a polymer of the unsaturated compounds, and a bottom liquid 22 of a heater, which contains metal acetates distilled from the catalyst, are drained out of a reaction process system from a column bottom of the heater 10 as a waste liquid in this example. On the other hand, a top liquid 21, from which the high-boiling-point component has been separated, from the heater 10 contains acetic acid and water and is recycled to the reaction. Therefore, the top liquid is mixed with a feed liquid 16 to the first distillation column and returned to the first distillation column 9, and then fed to the oxidation reactor 5 via the acetic acid-water evaporator 4.

In that case, oxygen gas 1 is added to an outlet gas 11 evaporated by heating in the acetic acid-water evaporator 4, from a column top of the acetic acid-water evaporator 4, and then the gas is fed to the oxidation reactor 5 as a raw material gas 12.

Since such a process for producing allyl acetate includes a heating step of heating a process liquid containing a part of the acetic acid-containing liquid at 80 to 250° C., it is also possible to suppress a decrease in activity and selectivity of the catalyst with which the oxidation reactor 5 is packed and to prevent a decrease of lifetime of the catalyst also in the process of recycling the unreacted acetic acid in the reaction.

The acetic acid-containing liquid (a bottom liquid 18 of the first distillation column in this example) contains, in addition to the unreacted acetic acid, water as a reaction product and a trace amount of allyl acetate, components such as impurities (unsaturated compounds such as allyl acrylate and acrylic acid) by-produced in the reaction in the oxidation reactor 5, and raw materials. With respect to a standard boiling point of these components, while acetic acid has a standard boiling point of 118° C., water has a standard boiling point of 100° C., allyl acetate has a standard boiling point of 103° C., allyl acrylate has a standard boiling point of 122° C., and acrylic acid has a standard boiling point of 139° C. The standard boiling points of these components are close to each other and it is difficult to separate these components from the acetic acid-containing liquid by simple distillation. On the other hand, there are circumstances, when allyl acetate is produced from oxygen, acetic acid and propylene, it is desirable to recycle the unreacted acetic acid in the production of allyl acetate from the viewpoint of effective utilization of raw materials, energy saving and cost. Conventionally, the acetic acid-containing liquid was recycled to the acetic acid-water evaporator 4 without sufficiently removing impurities such as unsaturated compounds, and then mixed with other raw materials and fed to the oxidation reactor 5. According to such a conventional process, components other than acetic acid contained in the acetic acid-containing liquid, such as water, allyl acetate, allyl acrylate and acrylic acid are also evaporated in the acetic acid-water evaporator 4 and then fed to the oxidation reactor 5. The present inventors have found that unsaturated compounds such as allyl acrylate and acrylic acid serve as a catalyst poison of the catalyst in the production of allyl acetate, and shorten the lifetime or the like, and investigated a process which could prevent these unsaturated compounds from being recycled to the oxidation reactor 5 as much as possible.

As a result of intensive study, the present inventors have conceived in this example that, by feeding the acetic acid-containing liquid recovered from a column bottom of the first distillation column 9 to the acetic acid-water evaporator 4, drawing out a part of the liquid from the column bottom of the acetic acid-water evaporator 4, and heat-treating this by a heater 10 as a process liquid containing the acetic acid-containing liquid, allyl acrylate and acrylic acid contained in the acetic acid-containing liquid are able to undergo a reaction (polymerization) with each other, thereby converting into a high-molecular-weight compound such as an oligomer, that is, a high-boiling-point compound, and thus acetic acid and these high-boiling-point compounds are easily separated even by simple distillation in this heater 10 or acetic acid-water evaporator 4. As a result, the concentration of the unsaturated compound to be fed to the oxidation reactor 5 can be decreased without an accompanying decrease in the capability of the acetic acid-water evaporator 4 or a loss of acetic acid, and thus catalyst performance can be improved.

In this example, the acetic acid-containing liquid is recovered from the column bottom of the first distillation column 9. For example, the acetic acid-containing liquid may be recovered from an outlet of the oxidation reactor 5 and the recovered liquid may contain impurities (unsaturated compounds such as allyl acrylate and acrylic acid) by-produced in the reaction.

The heater 10 does not cause lift-up (a phenomenon of being fed to a reactor in the form of mist (a non-evaporated state)) generated by the influence of a circulated gas when compared with the acetic acid-water evaporator 4 used generally in an allyl acetate production process, and also has a simple structure without requiring trays and is capable of easily performing a running operation, and thus it is possible to heat a liquid component more efficiently. Therefore, it is possible to decrease the concentration of unsaturated compounds in the acetic acid-containing liquid more effectively.

Furthermore, the acetic acid-water evaporator 4, which is present in the pre-step of the oxidation reactor 5, is largely influenced by running conditions of the oxidation reactor 5. For example, since a circulation gas 15 flows into the acetic acid-water evaporator 4 and a reactor inlet gas 12 is obtained from the column top, it becomes necessary to increase the operating pressure in the acetic acid-water evaporator 4 to a pressure which is at least higher than that of the oxidation reactor 5, taking a differential pressure into consideration. Therefore, operating conditions of the acetic acid-water evaporator 4 are restricted. On the contrary, the heater 10 enables the acetic acid-containing liquid to be subjected to a heat treatment without being restricted by the running conditions of the reaction system The running conditions of the acetic acid-water evaporator 4 are specifically as follows: pressure: 0.3 MPaG to 1.0 MPaG, temperature: 80° C. to 140° C., and amount of a circulation gas which passes through the acetic acid-water evaporator: preferably 3 t/hour to 40 t/hour. Under these running conditions, acetic acid and these high-boiling-point compounds can be easily separated by the acetic acid-water evaporator 4 even when a bottom liquid 22 of the heater is not emitted out of the system.

There is no limitation on the amount of the acetic acid-containing liquid drawn out of the acetic acid-water evaporator 4 to the heater 10. A mass ratio of the amount of the acetic acid-containing liquid fed to the acetic acid-water evaporator 4 to the amount of the acetic acid-containing liquid drawn out to the heater 10, feed amount:drawn out amount, is preferably from 40:1 to 1:1, and more preferably from 10:1 to 2:1. When the drawn out amount exceeds the above range, heating energy (amount of steam used) in the acetic acid-water evaporator 4 becomes too high. In contrast, when the drawn out amount is less than the above range, the concentrations of acrylic acid and allyl acrylate in the acetic acid-water evaporator 4 increase, and thus it may become impossible to sufficiently suppress deterioration of the catalyst in the oxidation reactor 5.

There is no particular limitation on the form of the heater 10, as long as the heater is a device capable of heating a liquid. It is preferable that a feed liquid can be condensed by heating an acetic acid-containing liquid and evaporating a part of the acetic acid-containing liquid.

Specifically, it is preferable to use an evaporator. Examples of a specific type of evaporator include a direct fire-type, a submerged combustion-type, a jacket-type, a natural circulation-type, a horizontal natural circulation-type, a vertical short-tube natural circulation-type, a vertical long-tube lifting film-type, a horizontal tube falling film-type, a vertical long-tube falling film-type, a horizontal tube forced circulation-type, a vertical tube forced circulation-type, a coil-type, a plate-type, a agitated film-type, a centrifugation-type and a flash evaporation-type (details thereof can be referred to, for example, "Kagaku Kogaku Binran (Handbook of Chemical Engineering", published by Maruzen Co., Ltd., Mar. 18, 1988, revised 5th edition, p. 395-, Item of "7 Evaporation"). Furthermore, a heat exchanger can be employed as the type of the heater 10, and a combination of a heat exchanger and a distillation column can also be employed. Examples of the heat exchanger include a multi-tube cylindrical-type heat exchanger, a spiral tube-type heat exchanger, a spiral plate-type heat exchanger, a plate-type heat exchanger, a double tube-type heat exchanger, a liquid film-type heat exchanger, a foam contact-type heat exchanger, a multi-concentric cylindrical-type heat exchanger, a scraped-surface-type heat exchanger, a scraped-surface liquid film-type heat exchanger, a centrifugal thin-film-type heat exchanger, a tank coil-type heat exchanger and a tank jacket-type heat exchanger (these heat exchangers are referred to in "Heat Exchanger Design Handbook (enlarged and revised edition)", Kougakutosho Ltd., published on Jan. 25, 1974, 2nd edition, 5th printing).

It is also possible for two or more sequences of heaters 10 to be used and arranged in any one of a series, parallel, or a combination of series and parallel, and each sequence is operated under various running conditions. In the case of two or more sequences of heaters 10, it is desirable that heat exchangers not be simultaneously used, but alternately used. In that case, in the case of switching to running of the other sequence after using one heater 10 for a given period, it becomes possible to perform continuous running without stopping running of the heater 10 when alkali water having the pH of 10 or more or steam is passed through the heater 10 used for a given period. There is no particular limitation on the switching time of running of the heater 10, and switching is preferably performed every 1,000 hours to 5,000 hours.

There is no particular limitation on the operating pressure of the heater 10, and it is possible to operate under conditions from a reduced pressure to an elevated pressure. The running pressure is preferably within a range from −0.1 to 10.0 MPaG, and more preferably from −0.02 to 1.0 MPaG. When the pressure is less than the above range, condensation of a column top component of the heater 10 tends to require energy. In contrast, when the pressure exceeds the above range, it becomes difficult to separate a low-boiling component and a high-boiling component, and high cost is required from the viewpoint of the device specification and material.

There is no particular limitation on the material of an acetic acid heater 10, and the acetic acid heater is preferably constituted of a material having corrosion resistance.

In the example of FIG. 1, the top liquid 21 of the heater 10 is fed to the first distillation column 9 for recycling. As long as acetic acid contained therein is fed to the oxidation reactor 5 via the acetic acid-water evaporator 4, the destination for feed is not limited thereto and acetic acid may be fed to any step of an acetate production process. Generally, in a process for producing allyl acetate, a pressure of a reaction step to a middle tank 7 is high, and the concentrations of acetic acid and water in the middle tank 7 and the downstream side thereof are comparatively high. Therefore, from the viewpoint of quality of allyl acetate and an allyl alcohol product using the same, it is desirable that the top liquid 21 be fed to the first distillation column 9 like the example of FIG. 1, specifically, a line of a feed liquid 16 to the first distillation column 9.

The bottom liquid 22 of the heater 10 contains acetic acid, water, a high-boiling-point component, an acetate and the like. Particularly, when the high-boiling-point component and acetate are recycled to an allyl acetate production process, clogging of a process piping may arise. Therefore, like this example, it is desirable that the bottom liquid 22 be emitted and discharged out of the production step. In this case, there is no limitation on a flow rate of the bottom liquid 22 of the heater 10. A mass ratio of a outlet liquid 20 from a bottom of the acetic acid evaporator to the bottom liquid 22 of heater, is preferably within a range from 2:1 to 1,000:1, and more preferably from 20:1 to 500:1. When the flow rate of the bottom liquid 22 exceeds the above range, the amount of the bottom liquid to be emitted and discharged increases, resulting in a loss of acetic acid. In contrast, when the flow rate of the bottom liquid 22 is less than the above range, an increase in viscosity of the bottom liquid 22 arises and, in some cases, efficiency of the heater 10 may decrease.

As described above, it is preferable that the bottom liquid 22 of the heater 10 is directly emitted out of the system from the heater 10. Since a high-boiling-point compound contained therein has a boiling point, which is quite different from that of acetic acid, the bottom liquid 22 is not necessarily emitted directly out of the system from the heater 10 and may be fed to the other distillator. In the bottom liquid 22 of the heater 10, a boiling point of impurities is increased. Therefore, impurities remain by simple distillation in the heater 10 or acetic acid-water evaporator 4, and are not substantially contained in an outlet gas 11 from a column top of the acetic acid-water evaporator 4. It is necessary that these impurities be emitted out of the system in any step of the process.

There is no particular limitation on a residence time of a process liquid in the heater 10, and the residence time is preferably 5 minutes or more. The residence time is more preferably between 5.0 minutes and 90 minutes, and still more preferably between 5.0 minutes and 45 minutes. When the residence time is less than the above range, it is impossible to sufficiently react the unsaturated compounds in the acetic acid-containing liquid contained in the process liquid. As a result, the unsaturated compounds are not sufficiently separated and may be recycled to the oxidation reactor 5. In contrast, when the residence time exceeds the above range, it becomes necessary to increase the volume of the heater 10, resulting in a problem from the viewpoint of arrangement of the device and material cost of the device.

Herein, the residence time means the time during which a substance, which flows into and flows out of a certain finite space, resides in the space. A residence time (τ) is represented by the following equation:

$$\tau \text{ (hr)} = V/\theta$$

where $V$ (m$^3$) denotes a volume of a space, and $\theta$ (m$^3$/hr) denotes a volume flow rate of a substance which flows into the space.

Details thereof can be referred to, for example, VSHIN-PAN KAGAKU KOGAKU JITEN (New Edition, Dictionary of Chemical Engineering) edited by The Society for Chemical Engineers, Japan, published by Maruzen Co., Ltd., edited by May 30, 1974, p. 259.

An operating temperature (heating temperature) of the heater 10 is preferably from 80 to 250° C., and more preferably from 100 to 150° C., in terms of the liquid temperature of a column bottom of the heater 10. When the operating temperature is lower than the above range, it may become impossible to sufficiently react the unsaturated compounds. In contrast, when the operating temperature is higher than the above range, it may become difficult to ensure heat resistance and a heat source of the device. There is no particular limitation on the heat source of the heater 10, and any heat source such as steam and electricity can be used. There is also no particular limitation on the heating process.

A process for producing allyl acetate of another example will be described with reference to FIG. 2.

Figure 2:
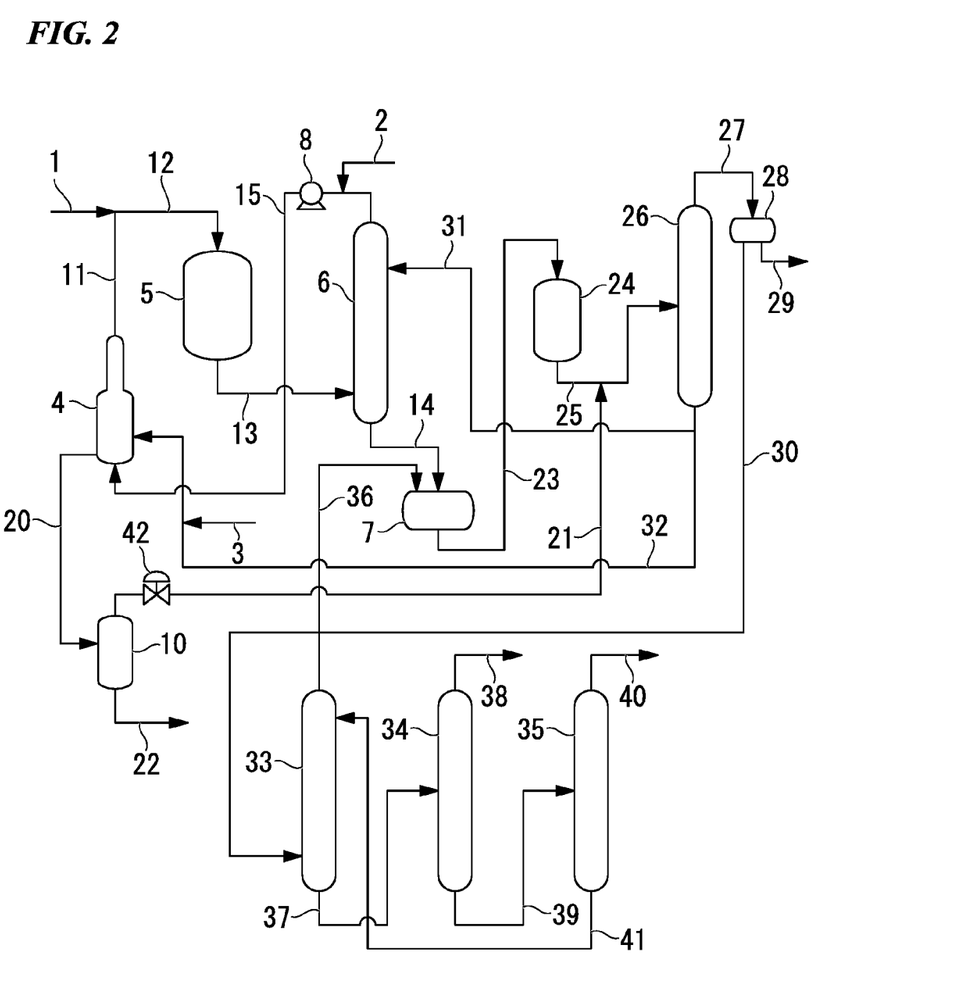
FIG. 2 is a process diagram showing another example of a production process of the present invention.

FIG. 2 shows a process further including a step of producing an aqueous 70% by mass allyl alcohol solution by hydrolyzing allyl acetate produced using a hydrolysis reactor 24. When allyl acetate produced by reacting oxygen, acetic acid and propylene is subsequently hydrolyzed to produce allyl alcohol, allyl acetate separated and distilled by the first distillation column 9 shown in FIG. 1 may be fed to the hydrolysis reactor. In the example of FIG. 2, a reaction mixed liquid (a bottom liquid 14 of a gas-liquid separator column) is fed through a middle tank 7 to a hydrolysis reactor 24 without separating and purifying allyl acetate. In FIG. 2, 26 denotes a second distillation column, and a reaction liquid 25 from the hydrolysis reactor 24 is distilled and separated into a bottom liquid of a second distillation column, and a top liquid 27 of a second distillation column. A bottom liquid of a second distillation column contains an acetic acid (comprising the unreacted acetic acid and acetic acid produced by hydrolysis), water and the other high-boiling point components. A top liquid 27 of a second distillation column is a mixture of allyl alcohol, allyl acetate and water.

In the process shown in FIG. 2, a bottom liquid (for recovery) 32 of a second distillation column is recovered to an acetic acid-water evaporator 4 as an acetic acid-containing liquid. A part of the bottom liquid of the second distillation column is fed, as a bottom liquid (for absorption) 31 of a second distillation column, to a gas-liquid separator 6 as absorption water.

The reaction scheme in the case of hydrolyzing allyl acetate to produce allyl alcohol is shown below.

$$CH_2=CH-CH_2-OCOCH_3+H_2O \rightarrow CH_2=CH-CH_2OH+CH_3COOH$$

There is no particular limitation on a pressure of a hydrolysis reaction, and the hydrolysis reaction can be performed under the pressure of 0.0 to 1.0 MPaG. There is also no particular limitation on a reaction temperature, the hydrolysis reaction is preferably performed at the reaction temperature of 20 to 300° C., and more preferably 50 to 250° C., so as to obtain a sufficient reaction rate.

There is no particular limitation on a reaction form of the hydrolysis reaction, and the hydrolysis reaction can be performed in any reaction form such as a vapor phase reaction, a liquid phase reaction and a coagulation reaction. The reaction form is preferably a vapor phase reaction or a liquid phase reaction.

There is equilibrium in a reaction between allyl acetate and water as raw material compounds in the hydrolysis reaction, and allyl alcohol and acetic acid as products of the hydrolysis reaction. In order to obtain a sufficient allyl acetate conversion ratio, the hydrolysis reaction is preferably performed by adding water. There is no particular limitation on the amount of water added, and the concentration of water in the raw materials is preferably from 1.0 to 60% by mass, and more preferably from 5 to 40% by mass. It is preferable that the reaction be performed while removing the product from the reaction system at any time so that equilibrium of the reaction becomes advantageous to the product side, using a generally known process. There is no particular limitation on the process of removing the product out of the reaction system, and examples of the process include a process in which a compound capable of forming an azeotropic mixture with allyl alcohol, like reactive distillation, is added and allyl alcohol is removed out of the reaction system while distillation is performed during the reaction.

In the hydrolysis reaction, the hydrolysis reaction of allyl acetate can be performed using only allyl acetate and water as raw compounds, and acetic acid and allyl alcohol as products. In order to obtain a sufficient reaction rate, the hydrolysis reaction of allyl acetate is preferably performed in the presence of an ester hydrolysis catalyst.

Examples of the hydrolysis catalyst of allyl acetate include, but are not limited to, an acidic substance and a basic substance.

The acidic substance is preferably an organic acid, an inorganic acid, a solid acid, and a salt thereof. Specific examples of the organic acid include formic acid, acetic acid, propionic acid, tartaric acid, oxalic acid, butyric acid, terephthalic acid, fumaric acid and the like. Examples of the inorganic acid include heteropoly-acid, hydrochloric acid, sulfuric acid, nitric acid, phosphoric acid, hydrobromic acid, hydrofluoric acid and the like. Examples of the solid acid include silica alumina, silica titania, silica magnesia, an acidic cation-exchange resin and the like, and examples of the salt thereof include a sodium salt, a potassium salt, a magnesium salt and an aluminum salt.

There is no particular limitation on the basic substance, and is preferably sodium hydroxide, potassium hydroxide, magnesium hydroxide, magnesium oxide, calcium oxide, an alkali anion-exchange resin and the like.

The acidic substance and the basic substance may be used alone, or at least two or more kinds thereof may be used in combination.

After the hydrolysis reaction of allyl acetate, it becomes necessary to separate the catalyst from allyl alcohol and acetic acid.

When a homogeneous catalyst such as sulfuric acid is used as a hydrolysis catalyst, it is necessary to separate allyl alcohol and acetic acid, and sulfuric acid from the uniform reaction mixture, and a large amount of energy is required. On the other hand, when a solid catalyst typified by an acidic cation-exchange resin is used, it is possible to separate catalyst, and allyl alcohol and acetic acid from the reaction mixture by a simple process such as filtration. Therefore, it is more preferable to hydrolyze by a heterogeneous catalytic reaction using a solid catalyst as an allyl acetate hydrolysis catalyst. The solid catalyst such as an acidic cation-exchange resin has high acidity and exhibits a satisfactory allyl acetate hydrolysis rate and long lifetime of the catalyst, and is most preferable as the hydrolysis catalyst.

Examples of the acidic cation-exchange resin include a sulfonated copolymer of styrene and divinylbenzene.

There is no particular limitation on a hydrolysis reactor 24. A fixed bed flow reactor is preferable. In case of the fixed bed flow reactor, the reaction mixture containing no acidic cation-exchange resin can be easily obtained from a reactor outlet while retaining the acidic cation-exchange resin in the reactor.

When allyl alcohol is produced using, as the reactor 24, a fixed bed flow reactor in which the acidic cation-exchange resin is used as the hydrolysis catalyst, there is no particular limitation on the direction in which a reaction starting liquid containing allyl acetate and water, that is, a hydrolysis reactor feed liquid denoted by 23 in FIG. 2 is passed, and the liquid may be passed by a downflow from the upper portion of a fixed bed flow reactor, or may be passed by an upflow from the lower portion.

In the case of the process for passing a hydrolysis reactor feed liquid 23 by a downflow from the upper portion of the reactor 24, the hydrolysis reactor feed liquid 23 can pass through the reactor 24 by dead weight and it is suitable since a power such as a pump is not required. However, in case of this process, there may arise a phenomenon such as a decrease in a reaction rate due to aggregation of an ion-exchange resin, drift of the hydrolysis reactor feed liquid 23 or the like, or an increase in pressure loss in the reactor 24, depending on the conditions. As a simple process for suppressing or dissolving such a phenomenon, a process of temporarily passing the hydrolysis reactor feed liquid 23 through the reactor 24 by an upflow from the lower portion of the reactor 24 is effective.

It is also preferable to use two or more reactors 24 in parallel since a given amount of allyl alcohol is continuously obtained.

In FIG. 2, a reaction liquid 25, which contains allyl alcohol, allyl acetate, acetic acid and water as main components, leaving from a hydrolysis reactor 24 is distilled and separated into a high-boiling-point component and a low boiling point component in a second distillation column 26, as described above. The high-boiling point component contains an acetic acid, water, and the other components. The low boiling-point component is a mixture of allyl alcohol, allyl acetate and water. Acetic acid and the high-boiling-point component are recovered as an acetic acid-containing liquid and then recycled to an acetic acid-water evaporator 4. A part of acetic acid and the high-boiling-point component is fed to a gas-liquid separator 6.

In the acetic acid-water evaporator 4, a part of a bottom liquid is drawn out as an outlet liquid 20 and then fed to a heater 10 as a process liquid containing an acetic acid-containing liquid, in the same manner as in the example of FIG. 1. And thus unsaturated compounds such as allyl acrylate and acrylic acid acting as a catalyst poison, which are contained in the liquid 20 also, undergo a reaction (polymerization) to form a high-boiling-point component (heating step). Then, a bottom liquid 22 of a heater, which contains the high-boiling-point component composed of a polymer of these unsaturated compounds, and acetates distilled from the catalyst, is emitted out of a reaction process system from a column bottom of the heater 10 as a waste liquid in this example. On the other hand, a top liquid 21, from which the high-boiling-point component has been separated, from the heater 10 contains acetic acid and water and is mixed with a reaction solution 25 and returned to the second distillation column 26, and then fed to the oxidation reactor 5 via the acetic acid-water evaporator 4.

In that case, oxygen 1 is added to an outlet gas 11 from the column top of the acetic acid-water evaporator 4, and then the gas is fed to the oxidation reactor 5 as a raw material gas 12. Reference number 42 denotes a pressure control valve, whereby, a pressure of the heater 10 can be controlled.

On the other hand, a top liquid 27 of a second distillation column is transferred to a decanter 28, where the top liquid is separated into two layers of an oil layer and an aqueous layer. An oil layer 30 having a high content of allyl acetate is introduced into an extraction column 33. A bottom liquid 37 of the extraction column 33 is introduced into a third distillation column 34 and distilled, and a bottom liquid 39 of a third distillation column (a mixed solution of water and allyl alcohol) is drawn out of the column bottom of the third distillation column 34. A part of a top liquid 36 of an extraction column 33, which contains allyl acetate obtained from the column top of the extraction column 33 as a main component and has a decreased concentration of allyl alcohol, is circulated into a hydrolysis reactor 24. The bottom liquid 39 of the third distillation drawn out of the column bottom of the third distillation column 34 is introduced into a fourth distillation column 35 and distilled to obtain 70% by mass of an allyl alcohol product concentrated as an azeotrope of water and allyl alcohol from the column top of the fourth distillation column 35, that is, a top liquid 40 of a fourth distillation column. A bottom liquid 41 (water) of a fourth distillation column drawn out of the column bottom of the fourth distillation column 35 is circulated as extraction water of the extraction column 33. In FIG. 2, 38 denotes a top liquid of a third distillation column, which contains allyl acetate, water and a low boiling-point component.

According to the process in FIG. 2, acetic acid thus by-produced in the process for producing allyl alcohol by hydrolysis of allyl acetate is recycled together with the unreacted acetic acid from the oxidation reactor 5.

In this case, a bottom liquid (for recovery) 32 of a second distillation column, as the acetic acid-containing liquid, contains components other than acetic acid, such as impurities (unsaturated compounds such as allyl acrylate and acrylic acid) by-produced by the hydrolysis reaction of allyl acetate, and raw materials, and is recycled via a heating step using a heater 10. Therefore, in the same manner as in the example of FIG. 1, it is possible to suppress recycling of these unsaturated compounds to the oxidation reactor 5 and to prevent a decrease of lifetime of the catalyst.

In case of the example of FIG. 2, a top liquid 21 of the heater 10 is returned to a second distillation column 26 for recycling, but is not limited thereto. As long as acetic acid contained therein is fed to the oxidation reactor 5 through an acetic acid-water evaporator 4, the top liquid 21 may be fed to any step of an allyl acetate production process shown in FIG. 2. From the viewpoint of quality of allyl acetate and allyl alcohol, it is desirable that the top liquid 21 be fed to the second distillation column 26 like the example of FIG. 2, specifically, a line of feeding a reaction solution 25 to the second distillation column 26.

In the example of FIG. 1, a liquid containing the unreacted acetic acid in the reaction of oxygen, acetic acid and propylene is recovered as the acetic acid-containing liquid. On the other hand, in the example of FIG. 2, a liquid containing acetic acid by-produced in the process for hydrolysis of allyl acetate and the unreacted acetic acid is recovered as the acetic acid-containing liquid.

However, the acetic acid-containing liquid may contain only acetic acid by-produced in the process for hydrolysis of allyl acetate.

According to the production process of the present invention described in detail above, in case oxygen, acetic acid and propylene are reacted in the presence of a catalyst to produce allyl acetate and water, when an acetic acid-containing liquid is recovered and recycled for the reaction via an acetic acid-water evaporator, a heating step of heating a process liquid containing the acetic acid-containing liquid thus recovered by a heater is performed. Therefore, activity and selectivity of the catalyst used in the production of allyl acetate are enhanced and, furthermore, lifetime elongation of the catalyst is achieved. It is also possible to produce allyl acetate and to produce allyl alcohol by hydrolysis reaction of allyl acetate, with higher efficiency.

EXAMPLES

The present invention will be specifically described below by way of Examples and Comparative Examples, but the present invention is not limited to these Examples.

Example 1

To 346 L of an aqueous solution containing 11.1 kg of sodium tetrachloropalladate ($Na_2PdCl_4$) and 1.5 kg of copper chloride dihydrate ($CuCl_2 \cdot 2H_2O$), 1,000 L of a silica spherical carrier having a particle size of 5 mm (spherical diameter: 5 mm, specific surface area: 155 $m^2$/g, HSV-I manufactured by Shanghai Haiyuan Chemical Industry Science Technology Co., Ltd.) was added, thereby completely impregnating the silica spherical carrier with the solution. Next, this silica spherical carrier was added to 730 L of an aqueous solution containing 39.1 kg of sodium metasilicate nonahydrate (Na$_2$SiO$_3$.9H$_2$O) and then subjected to an alkali treatment at room temperature for 20 hours.

Then, hydrazine hydrate was added and then the silica spherical carrier was subjected to a reduction treatment. After reduction, the silica spherical carrier was washed with water until chlorine ions are not detected. Next, the silica spherical carrier was dried at 110° C. for 4 hours. Furthermore, the silica spherical carrier was introduced into 328 L of an aqueous solution containing 45 kg of potassium acetate (KOAc) and, after absorption of the entire solution, the silica spherical carrier was dried again at 110° C. for 20 hours.

This operation was repeated to obtain several m$^3$ of a catalyst for producing allyl acetate (catalyst A).

In the production process shown in FIG. 2, an oxidation reactor 5 was packed with the catalyst for producing allyl acetate (catalyst A) produced by the above process and a raw material gas (oxidation reactor feed gas) 12 comprising a condensable component (23,000 kg/hour) containing acetic acid and water as main components, propylene (36,000 kg/hour), oxygen (5,000 kg/hour), and a nitrogen gas as an inert gas was fed while adjusting a flow rate so that a space velocity of total gas becomes 2,000 hour$^{-1}$. Also, the reaction temperature was adjusted so that the feed amount of 3,000 kg/hour of oxygen 1 is consumed in the oxidation reactor 5, and an oxidation reaction was performed under the conditions of a reaction pressure of 0.75 MPaG.

Next, an outlet gas 13 of the oxidation reactor 5 was fed to a gas-liquid separator (gas-liquid separation column) 6, and a bottom liquid (for absorption) 31 of a second distillation column, which contains acetic acid and water as main components, was used as an absorption liquid. Then, a non-condensable component containing propylene, oxygen gas and a carbon dioxide gas as main components was separated from a column top and circulated to the oxidation reactor 5 via an acetic acid-water evaporator 4. On the other hand, a bottom liquid 14 of the gas-liquid separator column, which contains acetic acid, water, allyl acetate and others as condensable components, was obtained.

To a hydrolysis reactor 24 packed with an ion-exchange resin (strong acidic cation-exchange resin (manufactured by ORGANO CORPORATION under the trade name of AMBERLYST31WET)) as a catalyst for producing allyl alcohol, a mixed solution (hydrolysis reactor feed liquid 23) of a bottom liquid 14 of the gas-liquid separator column and a top liquid 36 of an extraction column was circulated under the conditions of a reaction temperature of 85° C. and a hydrolysis reaction of allyl acetate was performed.

Next, a distillation operation was performed in a second distillation column 26 for the purpose of separating acetic acid from a reaction solution (outlet liquid) 25 containing allyl alcohol, allyl acetate, acetic acid and water as main components of the hydrolysis reactor 24. In the distillation operation, running conditions were adjusted so that the concentration of water in the bottom liquid of the second distillation column 26 becomes 40% by mass. A top liquid 27 of a second distillation column was separated into an allyl acetate-rich oil layer 30 and an aqueous layer 29 by decantation.

In an extraction column 33, allyl alcohol in an oil layer 30 was extracted using, as extraction water, a bottom liquid 41 of a fourth distillation column, which contains water as a main component. The oil layer (a top liquid 36 of an extraction column) containing allyl acetate as a main component obtained from the column top was circulated again to the above hydrolysis reactor 24.

A bottom liquid 37 of the extraction column 33 was fed to a third distillation column 34 and a low boiling point component contained therein was removed by separation from the column top, and a liquid (a bottom liquid 39 of a third distillation column) containing allyl alcohol and water as main components was obtained from the column bottom.

In a fourth distillation column 35, a bottom liquid 39 of a third distillation column was distilled, and an aqueous 70% by mass allyl alcohol solution (allyl alcohol product; a top liquid 40 of a fourth distillation column) was obtained from the column top. A part of a bottom liquid 41 of a fourth distillation column was recycled to the extraction column 33 and utilized as extraction water, and the remainder was circulated to a reactor for producing allyl alcohol.

Among a bottom liquid of a second distillation column, a bottom liquid (for recovery) 32 of the second distillation column was recycled, as an acetic acid-containing liquid, to the acetic acid-water evaporator 4 in the amount of 29,000 kg/hour.

In the acetic acid-water evaporator 4, an operation was performed at a pressure of 0.85 MPaG and a column bottom temperature of 118° C., and an outlet liquid 20 from a bottom of the acetic acid-water evaporator was drawn out of the column bottom at a flow rate of 6,000 kg/hour and then fed to a heater 10. In the heater 10, a heating step was performed so that a residence time becomes 20 minutes and a column bottom temperature becomes 120° C., and a heater bottom liquid 23 was drained out of the system at 30 kg/hour from the column bottom of the heater 10. The remainder was fed to the second distillation column 26 as a heater top liquid 21. The heater 10 in the present Example is a simple evaporator.

Then, a part of a raw material gas (reactor inlet gas) 12 was introduced into a sampling device equipped with a cooler and a condenser, and 10 L of a reactor inlet gas condensate liquid A was collected. The concentration of acrylic acid in this reactor inlet gas condensate liquid A was 200 ppm by weight.

(Evaluation)

Next, using the reactor inlet gas condensate liquid A obtained by the above sampling, the reaction of a catalyst for producing allyl acetate (catalyst A) was evaluated. Specifically, 10.5 ml of the catalyst for producing allyl acetate A was uniformly mixed with 31.5 ml of a silica carrier and then the catalyst was packed to a reaction tube (made of SUS316L). Under the conditions of a reaction temperature of 155° C. and a reaction pressure of 0.8 MPaG (gauge pressure), the reactor gas condensate liquid A was used as a raw material of acetic acid and a mixed gas obtained by mixing according to the gas composition [propylene:oxygen:acetic acid:mixture of nitrogen and water=30:6:7:57] was introduced at a space velocity of 2,100 hr$^{-1}$, and then an oxidation reaction was performed.

The total amount of an outlet gas passed through a catalyst packed layer is cooled and the total amount of a condensed reaction solution was recovered and then analyzed by a gas chromatography. The uncondensed gas, the total amount of the uncondensed gas was collected within a sampling time and a part thereof was analyzed by a gas chromatography.

The condensed reaction solution was analyzed by an internal standard method using GC-14B manufactured by Shimadzu Corporation, a FID detector and a capillary column TC-WAX (measuring 30 m in length, 0.25 mm in inner diameter and 0.25 μm in thickness). On the other hand, the uncondensed gas was analyzed by an absolute calibration curve method by gas chromatography (GC-14B, manufactured by Shimadzu Corporation) with a gas sampler (MGS-4, measuring tube: 1 ml) for Shimadzu gas chromatography, a TCD detector (He carrier gas, current 100 mA) and a packed column (measuring 3 mmφ×3 m) MS-5A IS (60/80 mesh).

Activity of the catalyst was calculated as a mass (space time yield: STY, unit: g/L-cat·hour) per hour per catalyst volume (liter) of allyl acetate produced.

Selectivity of allyl acetate was determined by the following calculation equation.

Allyl acetate selectivity(in terms of propylene) (%)=
[amount of allyl acetate produced (mol)/amount of propylene consumed (mol)]×100

Sampling was performed every several hours after initiation of the reaction and activity of the catalyst was determined from the analytical results.

On 4 hours after initiation of the reaction, allyl acetate STY was 274 g/L-cat·hour and allyl acetate selectivity was 91.9%. After reacting for 287 hours, allyl acetate STY was 163 g/L-cat·hour and allyl acetate selectivity was 91.0%.

Example 2

Evaluation

In the same manner as in Example 1, the oxidation reaction of oxygen, acetic acid and propylene was performed, except that the reaction temperature of 135° C. in place of the reaction temperature of 155° C. After reacting for 4 hours and 166 hours, sampling was performed and activity of the catalyst was determined from the analytical results.

Four hours after initiation of the reaction, allyl acetate STY was 97 g/L-cat·hour and allyl acetate selectivity was 90.3%. After reacting for 166 hours, allyl acetate STY was 75 g/L-cat·hour and allyl acetate selectivity was 89.0%.

Comparative Example 1

In the same manner as in Example 1, an allylacetate was produced except that among the bottom liquid of the second distillation column, a bottom liquid (for recovery) 32 of the second distillation column was recycled to an acetic acid-water evaporator 4 in the amount of 26,000 kg/hour. A bottom liquid of the acetic acid-water evaporator was drawn out of a bottom of the acetic acid-water evaporator 4 at a flow rate of 3,000 kg/hour. the pressure of a heater was controlled to an absolute pressure of 20 kPa by a pressure control valve 42 and heating was performed so that a column bottom temperature becomes 55° C., the bottom liquid 22 of the heater was extracted at 15 kg/hour, and the remainder was fed to a second distillation column 26 as a top liquid 21 of a heater.

In this case, a part of the raw material gas (reactor inlet gas) 12 was introduced into a sampling device equipped with a cooler and a condenser, and 10 L of a reactor inlet gas condensate liquid B was collected. The concentration of acrylic acid in this reactor inlet gas condensed component was 4,150 ppm.

In the same manner as in Example 1, except that this reactor inlet gas condensate liquid B was used, a catalyst for producing allyl acetate (catalyst A) was evaluated and sampling was performed every several hours after initiation of the reaction, and then activity of the catalyst was determined from the analytical results.

Four hours after initiation of the reaction, allyl acetate STY was 238 g/L-cat·hour and allyl acetate selectivity was 91.0%. After reacting for 287 hours, allyl acetate STY was 82 g/L-cat·hour and allyl acetate selectivity was 82.6%.

Comparative Example 2

In the same manner as in Example 1, an allyl acetate was produced except that among a bottom liquid of a second distillation column, a bottom liquid (for recovery) 32 of the second distillation column was recycled to an acetic acid-water evaporator 4 in the amount of 24,000 kg/hour. From bottom of the acetic acid evaporator 4, an outlet liquid 20 from a bottom of the acetic acid-water evaporator was drawn out at a flow rate of 1,000 kg/hour. The pressure of a heater was controlled to an absolute pressure of 20 kPa by a pressure control valve 42 and heating was performed so that a column bottom temperature becomes 55° C., the bottom liquid 22 of the heater was extracted at 10 kg/hour, and the remainder was fed to a second distillation column 26 as a top liquid 21 of a heater.

In this case, a part of a reactor inlet gas 12 was introduced into a sampling device equipped with a cooler and a condenser, and 10 L of a reactor inlet gas condensate liquid C was collected. The concentration of acrylic acid in this reactor inlet gas condensed component was 9,800 ppm.

In the same manner as in Example 1, except that this reactor inlet gas condensate liquid C was used, a catalyst for producing allyl acetate (catalyst A) was evaluated and sampling was performed on 4 hours and 166 hours after initiation of the reaction, and then activity of the catalyst was determined from the analytical results. Four hours after initiation of the reaction, allyl acetate STY was 74 g/L-cat·hour and allyl acetate selectivity was 84.1%. After reacting for 166 hours, allyl acetate STY was 30 g/L-cat·hour and allyl acetate selectivity was 75.2%.

Figure 3:
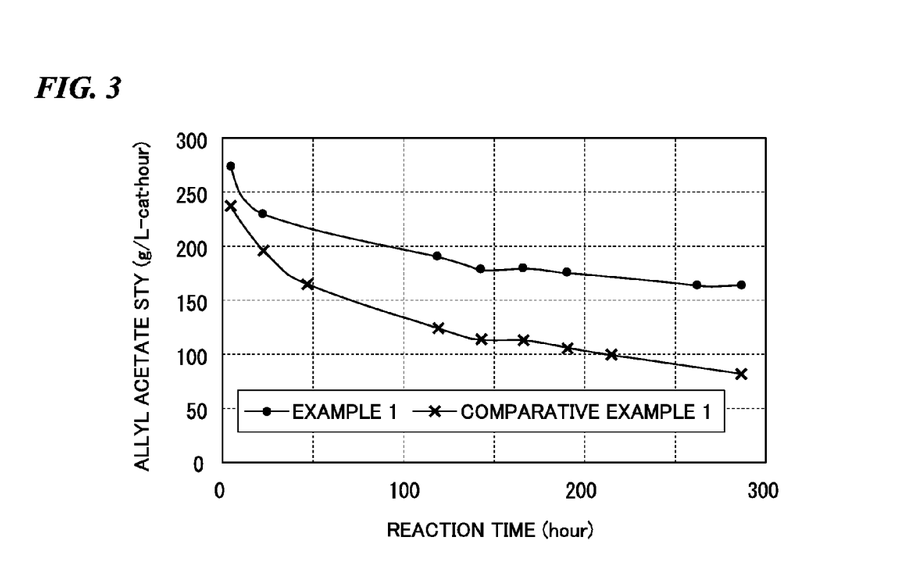
FIG. 3 is a graph showing the relationship between the reaction time and STY of allyl acetate in Example 1 and Comparative Example 1.
Figure 4:
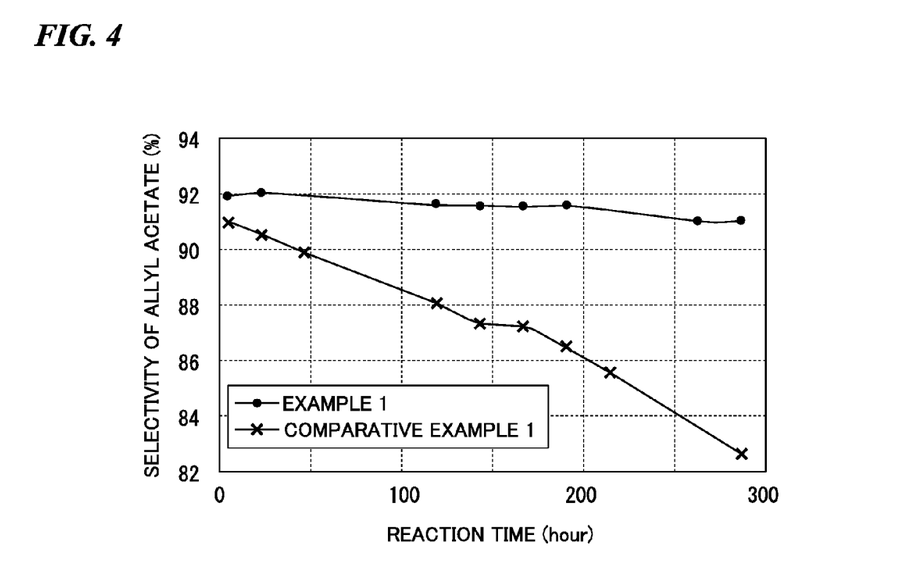
FIG. 4 is a graph showing the relationship between the reaction time and the selectivity of allyl acetate in Example 1 and Comparative Example 1.

The evaluation results are shown in Table 1. As is apparent from these results, the processes for producing allyl acetate of Examples 1 and 2 are excellent in activity and selectivity of the catalyst for producing allyl acetate when compared with the processes of Comparative Examples 1 and 2. Furthermore, as is apparent from FIG. 3 and FIG. 4, the catalyst of Example 1 exhibits a longer lifetime than that of the catalyst of Comparative Example 1.

TABLE 1

|  | Reaction time (hour) | Allyl acetate STY (g/L-cat · hour) | Acetic acid selectivity (%) |
| --- | --- | --- | --- |
| Example 1 | 4 | 274 | 91.9 |
|  | 287 | 163 | 91.0 |
| Example 2 | 4 | 97 | 90.3 |
|  | 166 | 75 | 88.8 |
| Comparative Example 1 | 4 | 238 | 91.0 |
|  | 287 | 82 | 82.6 |
| Comparative Example 2 | 4 | 74 | 84.1 |
|  | 166 | 30 | 75.2 |

REFERENCE SIGNS LIST

1: Oxygen
2: Propylene
3: Acetic acid
4: Acetic acid-water evaporator
5: Oxidation reactor
6: Gas-liquid separator
7: Middle tank
8: Compressor of circulation gas
9: First distillation column
10: Heater
11: Outlet gas of acetic acid-water evaporator
12: Raw material gas
13: Reactor outlet gas
14: Gas-liquid separator bottom liquid
15: Circulation gas
16: Feed liquid to first distillation column
17: Bottom liquid (for absorption) of first distillation column
18: Bottom liquid (for recovery) of first distillation column 19: Top liquid of first distillation column
20: Outlet liquid from a bottom of acetic acid-water evaporator
21: Top liquid of heater
22: Bottom liquid of heater
23: Hydrolysis reactor feed liquid
24: Hydrolysis reactor
25: Reaction liquid from hydrolysis reactor
26: Second distillation column
27: Top liquid of second distillation column
28: Decanter of second distillation column
29: Aqueous layer of top liquid of second distillation column
30: Oil layer of top liquid of second distillation column
31: Bottom liquid (for absorption) of second distillation column
32: Bottom liquid (for recovery) of second distillation column
33: Extraction column
34: Third distillation column
35: Fourth distillation column
36: Top liquid of extraction column
37: Bottom liquid of extraction column
38: Top liquid of third distillation column
39: Bottom liquid of third distillation column
40: Top liquid of fourth distillation column
41: Bottom liquid of fourth distillation column
42: Pressure control valve

What is claimed is:

1. A process for producing allyl acetate, comprising:
   reacting acetic acid, oxygen, and propylene in the presence of a catalyst in a reactor to produce allyl acetate and water;
   separating the unreacted acetic acid by a distillation column;
   recovering an acetic acid-containing liquid which contains acetic acid and returning the acetic acid-containing liquid to the reactor via an acetic acid-water evaporator; and
   heating a process liquid which contains the acetic acid-containing liquid to a temperature of 80 to 250° C. by a heater to polymerize unsaturated compounds,
   wherein the process liquid is the bottom liquid of the acetic acid-water evaporator.

2. The process for producing allyl acetate according to claim 1, wherein an evaporator is used as the heater.

3. The process for producing allyl acetate according to claim 1, wherein the process liquid after the heating is returned to the distillation column.

4. The process for producing allyl acetate according to claim 1, further comprising:
   hydrolyzing, before the separating, the allyl acetate; and
   supplying an acetic acid-containing liquid containing the acetic acid formed by the hydrolysis to the distillation column for the separating.

5. The process for production of allyl acetate according to claim 4, wherein the distillation column separates acetic acid formed by the hydrolysis.

6. The process for production of allyl acetate according to claim 1, wherein a heating temperature in the heater is from 100° C. to 150° C.

7. The process for production of allyl acetate according to claim 1, wherein a residence time in the heater is 5.0 minutes or more.

* * * * *